US00PP24138P3

(12) United States Plant Patent
Zaiger et al.

(10) Patent No.: US PP24,138 P3
(45) Date of Patent: Jan. 7, 2014

(54) INTERSPECIFIC TREE NAMED 'BELLA ZEE'

(50) Latin Name: **Interspecific *Prunus* species**
Varietal Denomination: Bella Zee

(76) Inventors: Gary Neil Zaiger, Modesto, CA (US); Leith Marie Gardner, Modesto, CA (US); Grant Gene Zaiger, Modesto, CA (US)

( * ) Notice: Subject to any disclaimer, the term of this patent is extended or adjusted under 35 U.S.C. 154(b) by 93 days.

(21) Appl. No.: 13/506,515

(22) Filed: Apr. 25, 2012

(65) Prior Publication Data

US 2013/0291237 P1 Oct. 31, 2013

(51) Int. Cl.
*A01H 5/00* (2006.01)

(52) U.S. Cl.
USPC ..... Plt./180

(58) Field of Classification Search
USPC ..... Plt./180
See application file for complete search history.

*Primary Examiner* — Annette Para

(57) ABSTRACT

A new and distinct variety of interspecific tree. The following features of the tree and its fruit are characterized with the tree budded on 'Nemaguard' Rootstock (non-patented), grown on Handford sandy loam soil with Storie Index rating 95, in USDA Hardiness Zone 9, near Modesto, Calif., with standard commercial fruit growing practices, such as pruning, thinning, spraying, irrigation and fertilization. Its novelty consist of the following combination of desirable features:

1. Fruit with attractive dark red skin color.
2. Fruit with good flavor and eating quality.
3. Regular and productive bearer of medium to large size fruit.
4. Fruit being relatively uniform in size and maturity throughout the tree.
5. Fruit with an average Brix of 22.5°.
6. Tree with vigorous, semi-spreading.

1 Drawing Sheet

Botanical designation: Interspecific *Prunus* species.
Variety denomination: 'Bella Zee'.

BACKGROUND OF THE VARIETY

1. Field of the Invention

In the field of plant genetics, we conduct an extensive and continuing plant-breeding program including the organization and asexual reproduction of orchard trees, and of which plums, peaches, nectarines, apricots, cherries, almonds and interspecifics are exemplary. It was against this background of our activities that the present variety of interspecific tree was originated and asexually reproduced by us in our experimental orchard located near Modesto, Stanislaus County, Calif.

2. Prior Varieties

Among the existing varieties of plum and interspecific trees, which are known to us, and mentioned herein, 'Friar' Plum (non-patented), 'Dapple Fire' Interspecific (U.S. Plant Pat. No. 12,409), the proprietary interspecific seedling selection '257LK9' (non-patented), the proprietary plum seedling selections '27EB180' (non-patented), '67GC150' (non-patented), '26GB440' (non-patented), '117GD279' (non-patented) and the proprietary plumcot seedling '4G1180' (non-patented).

STATEMENT REGARDING FEDERALLY SPONSORED RESEARCH AND DEVELOPMENT

Not applicable.

ORIGIN OF THE VARIETY

The present new and distinct variety of interspecific *Prunus* tree was originated by us from multiple crossing combinations of *Prunus salicina, Prunus armeniaca, Prunus persica* var. *nucipersica* and *Prunus persica*. It was originated by us in our experimental orchard located near Modesto, Calif. as a first generation cross between the proprietary interspecific seedling selection with the field identification number '257LK9' (non-patented) and 'Dapple Fire' Interspecific (U.S. Plant Pat. No. 12,409). The seed parent '257LK9' (non-patented) originated from crosses of the following varieties; 'Friar' Plum (non-patented), our proprietary plum seedlings '27EB180' (non-patented), '67GC150' (non-patented), '26GB440' (non-patented), '117GD279' (non-patented) and our proprietary plumcot seedling '4G1180' (non-patented). A large number of these first generation crosses were planted and grown on their own root system. Under close and careful observation one seedling, which is the present variety, exhibited desirable tree and fruit characteristics and was selected in 2002 for additional asexual propagation and commercialization.

ASEXUAL REPRODUCTION OF THE VARIETY

Asexual reproduction of the new and distinct variety of interspecific tree was by budding to 'Nemaguard' Rootstock (non-patented), as performed by us in our experimental orchard located near Modesto, Calif., and shows that reproductions run true to the original tree and all characteristics of the tree and its fruit are established and transmitted through succeeding asexual propagations.

SUMMARY OF THE NEW VARIETY

The new and distinct variety of interspecific tree [(Plum×Plumcot)×(Plum×Plum Nectarine))×(Peach×Plum Peach)] is of large size, semi-spreading growth and a regular and productive bearer of medium to large size fruit with good flavor and eating quality. The fruit is further characterized by having a very dark red skin color, being clingstone with firm flesh and an average Brix of 22.5°. In comparison to its seed parent '257LK9' interspecific (non-patented) the fruit of the new variety has sweeter flesh flavor and is approximately 60 days later in maturity. In comparison to its pollen parent 'Dapple Fire' Interspecific (U.S. Plant Pat. No. 12,409) the new variety has a darker red skin color, yellow flesh instead of dark red, pubescent skin compared to glabrous skin and is approximately 63 days later in maturity. In comparison to the commercial variety 'Black Kat' Interspecific (U.S. Plant Pat. No. 13,134) the fruit of the new variety has a darker yellow flesh color, pubescent skin compared to glabrous skin, a more elongated shape and is approximately 3 days earlier in maturity.

PHOTOGRAPH OF THE VARIETY

The accompanying color photographic illustration shows typical specimens of the foliage and fruit of the present new interspecific variety. The illustration shows the upper and lower surface of the leaves, an exterior and sectional view of a single fruit divided in its suture plane to show flesh color, pit cavity and the stone remaining in place. The photographic illustration was taken shortly after being picked (shipping ripe) from an 8 year old tree and the colors are as nearly true as is reasonably possible in a color representation of this type.

DESCRIPTION OF THE VARIETY

The following is a detailed botanical description of the new variety of interspecific tree, its flowers, foliage and fruit, as based on observations of 8 year old specimens grown near Modesto, Calif., with color in accordance with Munsell Book of Color.

Tree:

*Size*.—Large, usually pruned to 3 to 3.5 meters in height and width for economical harvesting of fruit. Varies with different types of soil and cultural practices.

*Vigor*.—Vigorous, tree growth of approximately 1.5 to 2 meters the first growing season. Varies slightly with cultural practices, soil type, fertility and climatic conditions.

*Form*.—Semi-spreading, usually pruned to vase shape.

*Branching habit*.—Semi-spreading, crotch angle approximately 35°, increases with heavy crop load.

*Productivity*.—Productive, thinning and spacing of fruit necessary for desired market size fruit. Fruit set varies with climatic conditions during bloom time.

*Bearer*.—Regular, adequate fruit set 6 consecutive years. No alternate bearing observed.

*Fertility*.—Self-sterile, pollinator required.

*Density*.—Medium dense, usually pruned to vase shape to increase sunlight to center of tree to enhance fruit color and health of fruit spurs.

*Hardiness*.—Hardy in all stone fruit growing areas of California. Tree grown in USDA Hardiness Zone 9. Winter chilling requirement approximately 1000 hours at or below 45° F.

Trunk:

*Size*.—Large, average circumference 48.3 cm at 25.4 cm above ground on a 8 year old tree.

*Stocky*.—Medium stocky.

*Texture*.—Medium shaggy, roughness increases with age.

*Color*.—Varies from 10YR 4/2 to 10YR 2/2.

Branches:

*Size*.—Medium. Average circumference 16.5 cm at 1.2 meters above ground. Crotch angle approximately 35°, increases with heavy crop load.

*Surface texture*.—New growth relatively smooth. Mature growth medium rough, roughness increases with age.

*Lenticels*.—Size — medium. Average length 4.0 mm. Average width 1.9 mm. Average number 30 in a 25.8 sq cm surface of branch. Color varies from 7.5YR 5/8 to 7.5YR 4/8.

*Color*.—New growth varies from 2.5GY 5/6 to 2.5GY 5/8. Old growth varies from 10YR 3/4 to 10YR 3/2, varies with age of growth.

Leaves:

*Size*.—Medium to large. Average length 101.6 mm. Average width 48.0 mm.

*Form*.—Oblanceolate.

*Apex*.—Acuminate.

*Base*.—Cuneate.

*Margin*.—Doubly serrate.

*Thickness*.—Medium.

*Surface texture*.—Upper surface relatively smooth, slightly indented over midrib and leaf veins. Lower surface relatively smooth, except for small ridges created by midrib and pinnate venation. Both surfaces glabrous.

*Petiole*.—Average length 15.3 mm. Average width 1.8 mm. Longitudinally grooved. Surface — glabrous. Color varies from 2.5GY 6/6 to 5R 3/8.

*Glands*.—Type — globose. Size — small. Average length 0.7 mm. Average diameter 0.4 mm. Number varies from 2 to 4, average number 3. Located primarily on base of leaf blade and upper portion of petiole. Color — 2.5GY 5/8.

*Stipules*.—Average number 2. Average length 7.6 mm. Margin — doubly serrate. Color 5GY 5/10.

*Color*.—Upper surface varies from 5GY 2/2 to 7.5GY 2/2. Lower surface varies from 2.5GY 3/2 to 5GY 3/4. Midvein color varies from 10Y 6/4 to 2.5GY 6/2.

Flower buds:

*Size*.—Small to medium. Average length 9.0 mm. Average diameter 3.6 mm.

*Hardiness*.—Hardy with respect to California winters.

*Form*.—Plump, conical, becomes elongated as bud matures.

*Pedicel*.—Average length 8.0 mm. Average width 1.0 mm. Color varies from 2.5GY 6/8 to 5GY 6/6. Surface — glabrous.

*Color*.—N 9.5/(white) with 2.5R 5/6 on some petal edges.

*Number of buds per spur*.—Average number 5, varies from 4 to 7.

Flowers:

*Blooming period*.—Date of First Bloom Mar. 3, 2011. Date of Petal Fall Mar. 16, 2011, varies slightly with climatic conditions.

*Size*.—Medium. Average height 11.7 mm. Average diameter 17.1 mm.

*Petals*.—Normally 5, alternately arranged to sepals. Size — medium. Average length 10.6 mm. Average width 6.0 mm. Form — elliptical. Margin — entire.

Color — N 9.5/(white) with 2.5R 8/2 on some petal edges, changes with age of flower. Both surfaces glabrous.

*Sepals*.—Normally 5, alternately arranged to petals. Size — small. Average length 2.2 mm. Average width 2.1 mm. Form — triangular. Margin — entire. Both surfaces glabrous. Color — upper surface varies from 2.5GY 6/8 to 5GY 5/6. Lower surface varies from 5GY 6/6 to 5GY 6/8.

*Stamens*.—Average number per flower 34. Average filament length 8.1 mm. Filament color N 9.5/(white). Anther color 10R 4/12 with 5Y 7/10.

*Pollen*.—Self sterile, pollinator required. Color varies from 5Y 7/10 to 5Y 7/12.

*Pistil*.—Normally 1. Surface pubescent. Average length 9.6 mm. Stigma height even with anthers. Color varies from 10Y 8/4 to 10Y 8/6.

*Fragrance*.—Heavy aroma.

*Color*.—N 9.5/(white) with 2.5R 8/2 on some petals outer edges.

*Number flowers per flower bud*.—Average number — 2, varies from 1 to 3.

*Pedicel*.—Average length 9.6 mm. Average width 1.0 mm. Color varies from 2.5GY 5/8 to 5GY 5/8. Surface — glabrous.

Fruit:

*Maturity when described*.—Firm ripe.

*Date of first picking*.—Sep. 4, 2011.

*Date of last picking*.—Sep. 13, 2011, varies slightly with climatic conditions.

*Size*.—Medium to large. Average diameter axially 64.1 mm. Average transversely in suture plane 58.8 mm. Average weight 139.2 grams, varies slightly with fertility of the soil, amount of thinning and climatic conditions.

*Form*.—Globose to slightly elongated.

*Suture*.—Nearly smooth, some fruit with slight suture. Extends from base to apex.

*Ventral surface*.—Nearly smooth, very slightly lipped.

*Apex*.—Varies from slightly rounded to flat.

*Base*.—Flat, varies from flat to slightly rounded.

*Stem cavity*.—Rounded to slightly elongated in suture plane. Average depth 1.4 mm. Average diameter 2.0 mm.

Stem:

*Size*.—Medium to large. Average length 16.0 mm. Average diameter 1.8 mm.

*Color*.—Varies from 10Y 6/6 to 2.5GY 7/6.

Flesh:

*Ripens*.—Evenly.

*Texture*.—Firm, meaty.

*Fibers*.—Few, small, tender.

*Firmness*.—Firm, comparable to other commercial varieties.

*Aroma*.—Slight.

*Amydgalin*.—Undetected.

*Eating quality*.—Good.

*Flavor*.—Good, good balance between acid and sugar.

*Juice*.—Heavy amount, enhances flavor.

*Brix*.—Average Brix 22.5°, varies slightly with amount of fruit per tree and climatic conditions.

*Color*.—Varies from 7.5YR 5/8 to 7.5YR 6/8.

*Pit cavity*.—Average length 27.0 mm. Average width 20.2 mm. Average depth 5.0 mm. Color varies from 10R 4/10 to 7.5R 4/10.

Skin:

*Thickness*.—Medium.

*Surface*.—Smooth.

*Pubescence*.—Moderate amount, very short.

*Tendency to crack*.—None.

*Color*.—Ground color varies from 10YR 6/6 to 2.5Y 6/4. Overspread with 2.5R 2/4 to 5R 2/2. Some fruit with small randomly spaced areas of ground color exposed to give a slight speckled pattern to some skin surface area.

*Tenacity*.—Tenacious to flesh.

*Astringency*.—None.

Stone:

*Type*.—Clingstone.

*Size*.—Medium to large. Average length 26.2 mm. Average width 19.6 mm. Average thickness 9.1 mm.

*Form*.—Ovoid.

*Base*.—Flat.

*Apex*.—Slightly pointed. Average length 1.3 mm.

*Surface*.—Slightly pitted throughout.

*Sides*.—Unequal, one side extending slightly further from suture plane.

*Ridges*.—A small, narrow ridge on each side of suture.

*Tendency to split*.—None.

*Color*.—Varies from 2.5YR 3/4 to 7.5YR 4/8 when dry.

Kernel:

*Size*.—Medium. Average length 15.9 mm. Average width 11.4 mm. Average depth 4.7 mm.

*Form*.—Ovate.

*Taste*.—Bitter.

*Viability*.—Viable, complete embryo development.

*Skin color*.—Varies from 7.5YR 4/6 to 7.5YR 4/8.

Use: Dessert.

*Market*.—Local and long distance.

Keeping quality: Good, held firm in cold storage 2 weeks at 38° to 42° F. without shriveling, internal breakdown of flesh or appreciable loss of eating quality.

Shipping quality: Good, showed minimal skin scarring or bruising during picking, packing and shipping trials.

Plant/fruit disease resistance/susceptibility: No specific testing for relative plant/fruit disease resistance/susceptibility has been designed. Under close observation during planting, growing, and harvesting of fruit, under normal cultural and growing conditions near Modesto, Calif., no particular plant/fruit disease resistance or susceptibility has been observed. Any variety or selection observed during indexing of plant characteristics with abnormal fungus, bacterial, virus or insect susceptibility is destroyed and eliminated from our breeding program.

The present new variety of interspecific tree, its flowers, foliage and fruit herein described may vary in slight detail due to climate, soil conditions and cultural practices under which the variety may be grown. The present description is that of the variety grown under the ecological conditions prevailing near Modesto, Calif.

The invention claimed is:

1. A new and distinct variety of interspecific tree, substantially as illustrated and described.

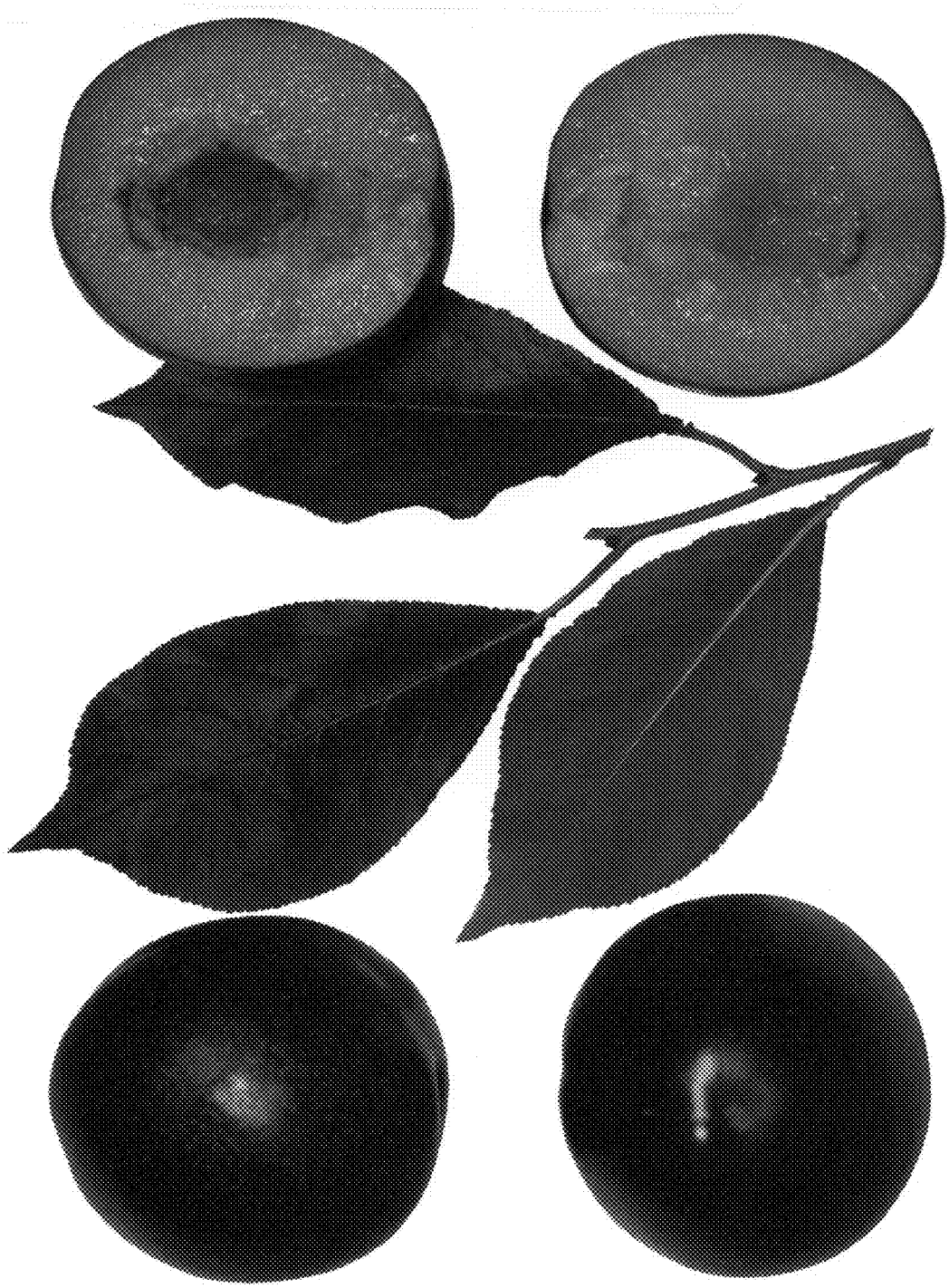

* * * * *